United States Patent [19]

Songer et al.

[11] Patent Number: 5,116,340
[45] Date of Patent: May 26, 1992

[54] SURGICAL SECURANCE APPARATUS

[76] Inventors: Robert J. Songer, 2104 Butternut, Northbrook, Ill. 60062; Matthew N. Songer, 2645 W. Grove St., Marquette, Mich. 49855

[21] Appl. No.: 564,749

[22] Filed: Aug. 9, 1990

Related U.S. Application Data

[62] Division of Ser. No. 301,728, Jan. 26, 1989, Pat. No. 4,966,600.

[51] Int. Cl.⁵ .............................................. A61B 17/56
[52] U.S. Cl. .................................... 606/103; 606/74; 29/282; 29/751
[58] Field of Search .................. 29/282, 283, 283.5, 29/750, 751; 72/409, 410; 606/74, 103; 81/418, 424.5, 426, 426.5

[56] References Cited

U.S. PATENT DOCUMENTS

| | | | |
|---|---|---|---|
| 2,291,413 | 7/1942 | Siebrandt | 606/103 |
| 3,111,945 | 11/1963 | Solbrig | 606/74 |
| 4,047,523 | 9/1977 | Hall | 606/61 |
| 4,050,464 | 9/1977 | Hall | 606/103 X |
| 4,128,100 | 12/1978 | Wendorff | 606/141 |
| 4,201,215 | 5/1980 | Gossett et al. | 606/74 X |
| 4,535,764 | 8/1985 | Ebert | 606/74 |
| 4,587,963 | 5/1986 | Leibinger et al. | 606/103 |
| 4,667,662 | 5/1987 | Titone et al. | 606/74 |
| 4,790,303 | 12/1988 | Steffee | 606/61 |
| 4,794,780 | 1/1989 | Battenfeld | 72/410 |
| 4,813,416 | 3/1989 | Pollack et al. | 606/151 |

FOREIGN PATENT DOCUMENTS

| | | |
|---|---|---|
| 126455 | 1/1948 | Australia . |
| 548197 | 10/1957 | Canada . |
| 2644735 | 4/1977 | Fed. Rep. of Germany . |
| 3146634 | 3/1986 | Fed. Rep. of Germany . |
| 543126 | 8/1922 | France ............... 606/103 |
| 7610576 | 9/1976 | Netherlands . |
| 425604 | 6/1967 | Switzerland . |
| 2207055 | 1/1989 | United Kingdom . |

OTHER PUBLICATIONS

Murray—Baumgarten Catalog, 1934.

Primary Examiner—Mickey Yu
Assistant Examiner—Kevin G. Rooney
Attorney, Agent, or Firm—Gerstman & Ellis, Ltd.

[57] ABSTRACT

A method for surgically securing body parts with a cable, typically making use of crimping pliers which comprises a pair of operating handles and connected, opposed jaws. The jaws define opposed recesses for carrying and crimping a tubular crimp member by manual pressure on the operating handles. A capstan is carried on one of the handles for winding a cable which passes through a tubular crimp member carried in the jaws. By this invention surgical cable may be looped around body parts in surgical operations, and the loop may be permanently secured at a predetermined desired tension.

20 Claims, 1 Drawing Sheet

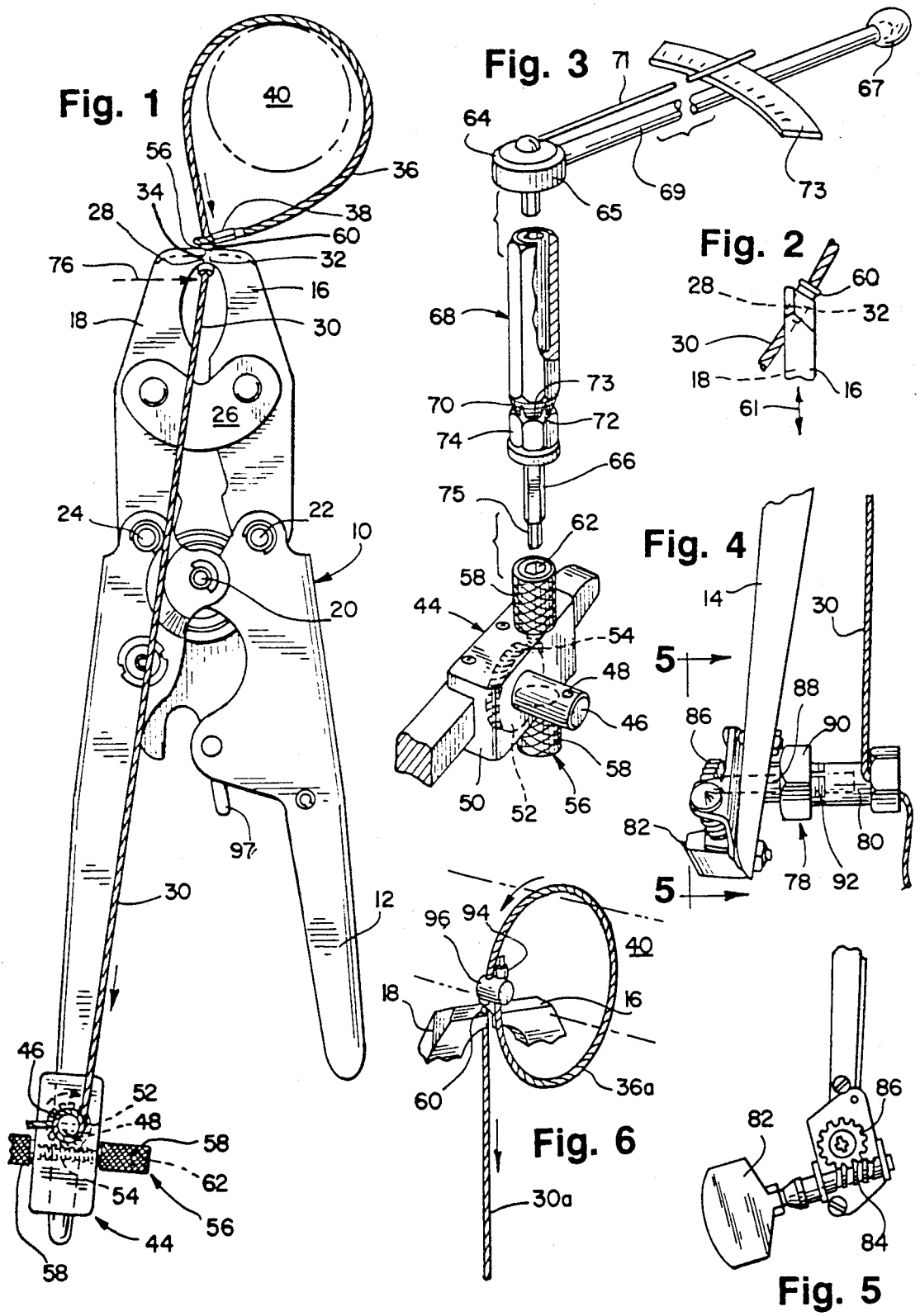

SURGICAL SECURANCE APPARATUS

This is a division of application Ser. No. 301,728, filed Jan. 26, 1989, now U.S. Pat. No. 4,966,600.

TECHNICAL FIELD

Surgical wires are used in a variety of surgical procedures, for example reconstructive spine surgery such as fusions, spine trauma surgery, total hip arthroplasty, fracture fixation, open heart surgery for closures of the sternum, oral/facial surgery to fix mandibular fractures and the like, and other trauma surgery. Often, surgical cable such as monofilament wire is used to encircle broken bones to hold them together for healing. Also, multifilament cable has been used.

Current systems for applying surgical cable (which word is intended to include single strand wire or multifilament cable) have problems in that surgical cables that are applied too tightly can create a vascular necrosis of the bone around which they are wrapped but they must be tight enough for proper mechanical fixation. It is a matter of difficulty to set the correct tension onto surgical cable at the time of installation. Also, with many conventional systems, the surgeon has great difficulty in doing all that needs to be done with only two hands as the cable is set in place and tensioned.

The Richards Company of Chattanooga, Tenn. manufactures a device for applying titanium cable in surgical procedures, with the cable loop being defined by a double-lumen crimp member in which the double-lumen passes longitudinally through the crimp member, which is in the form of a short rod. The titanium cable is placed through one of the lumens, and then is passed around the surgical repair site and back again through the other lumen to define the loop. In the Richards Company crimping device the crimp is positioned cross-wise in the crimping device in substantially perpendicular manner thereto. As a result of this, a large incision is required for the crimping device to be brought to bear at the surgical site. Also, a second, separate tensioning device is used, which adds to the complexity of the operation.

Furthermore, the loop of cable formed around the bone by the Richards system invariably forms a certain amount of slackness in the loop, since the outer end of the crimper jaws must pass around the circumference of the transverse crimp member between the transverse crimp member and the bone. Thus, an amount of slack is formed when the crimper is withdrawn.

In accordance with this invention, an improved method and apparatus are provided for use in the application of surgical cable loops in their wide variety of surgical uses. The disadvantages of the prior art are significantly reduced, in that it becomes possible to more easily apply a predetermined amount of tension to the cable loop about the bone to avoid excess tension, while at the same time the apparatus of this invention permits the formation of cable loops that are slack-free. Additionally, the application of the cable loops may be performed by a single surgeon with significantly reduced difficulty, and the crimping pliers in accordance with this invention are more easily inserted into a surgical incision to apply wiring at hard-to-reach places.

DESCRIPTION OF THE INVENTION

In this invention, a method is provided of surgically securing body parts with a cable, which comprises the following steps:

One forms a cable loop around the body parts, the loop of the cable being at substantially one cable end.

One places a tubular crimp member into crimping pliers either before or after the above mentioned step.

One then passes the cable end opposed to the one end through the tubular crimp member from front to rear.

One then connects the cable to a winding shaft carried on said pliers, with a cable portion between the opposed cable end and loop occupying the bore of the crimp member.

One then rotates the winding shaft to tighten the cable loop about the body part to a predetermined tightness.

Following this, one collapses the crimp member with the crimping pliers to secure the crimp member on the cable, while the crimp member is pressing against the loop, and is too large to pass through a joining connection of cable portions that defines the loop.

As a result of this, a permanent, desirably slackless, cable loop of predetermined tightness is formed about the body parts.

It may be desired for the cable to define a permanently looped eyelet end, with the cable loop referred to above being formed by having an intermediate cable portion extending through the looped eyelet end.

Following the collapsing step described above, one may cut the cable essentially flush with the crimp member at the crimp member end opposed to the looped end.

As one advantage of this invention, one may rotate the winding shaft to its predetermined tightness by means of a torque wrench. By this expedient, a precise, numerically valued tightness can be provided to the cable loop.

As another feature of this invention, the tubular crimp member is collapsed with the crimping pliers while it occupies an acute lateral angle to the axis of the pliers, rather than being substantially perpendicular or parallel thereto. Preferably, the acute lateral angle is from about 10 to 50 degrees, with the result that the cable goes into the cramping jaws at one end and comes out of the cramping jaws at the other end of the crimp member at an oblique angle, which is still conveniently directed toward the rear of the pliers, without difficulty. The cable is connected to a capstan which includes the winding shaft.

Because the crimp member faces generally forwardly of the pliers axis rather than substantially perpendicular to the pliers axis, the crimping takes place laterally around the crimp member while the forward end of the crimp member directly impinges the cable loop. Thus, by this means, slackless cable loops may be formed about bone.

Preferably, the tubular crimp member defines a circumferential flange about its front end, which prevents slippage in the pliers and facilitates the application of a tight loop as the rotating winding shaft tightens the cable to a predetermined tension, prior to crimping of the crimp member to permanently fix that tension in the cable loop.

Alternatively, the cable loop which is formed about bone at a surgical site in accordance with this invention may be defined with a bar member which defines a pair of spaced, transverse apertures. The cable extends through both apertures to define the loop, and is held therein by a permanent cable stop mounted on the cable adjacent its end. The stop is too large to pass through its associated transverse aperture and presses against it, while the tubular crimp member of this invention may be used to prevent withdrawal of the cable of the loop from the other transverse aperture.

The advantage of this structure is that the bar member tends to lie flat against the bone when the cable loop has been tensioned. Thus the projecting cable ends, after the remaining cable has been cut away do not project outwardly from the bone, but tend to project in the direction of a tangent line to the circumference of the bone.

Thus, by this method, surgical loops may be formed of cable for any of variety of desired purposes with great ease, with less chance for excessive cable pressure against the bone, while at the same time providing firm tension, and with greater ease.

Further in accordance with this invention, crimping pliers are provided which comprises a pair of operating handles and connected, opposed jaws, generally in the manner of conventional crimping pliers. The jaws define opposed recesses for carrying and crimping a tubular crimp member by manual pressure on the operating handles. Capstan means are carried on one of the handles for winding a cable which passes through a tubular crimp member carried in the jaws.

It is preferred for the opposed recesses to be positioned to carry the crimp member at an acute angle to the axis of the crimping pliers, but still generally forward-facing so that the front end of the crimp member can directly press against the cable loop. This acute angle is preferably about 10 to 50 degrees, most preferably about 15 to 30 degrees, to permit cable that exits from the rear of the crimp member to laterally clear the crimping jaws and to easily extend back along the crimping pliers to the capstan means.

The capstan means carried on the pliers of this invention preferably comprises a winding shaft for retaining and winding the cable, a rotatable handle, and gear means for rotating the winding shaft with rotation of the handle. It may be desired for the rotatable handle to define a connection for receiving wrench means, for example a hexagonal hole in its end. The wrench means used is preferably a torque wrench, so that the cable loop may be tightened by rotating of the capstan means to a precisely predetermined torque at which the tension of the wire loop is optimal for the specific surgical purpose. A typical torque tension used herein may be 20 pounds, and may be varied in accordance with the opinion of the surgeon.

Preferably, the rotatable handle of the capstan means extends outwardly from two opposed sides of the wrench operating handle that carries the capstan means, for rotation of the rotatable handle from either side. This facilitates the operation of the apparatus of this invention by the surgeon.

DESCRIPTION OF THE DRAWINGS

In the drawings, FIG. 1 is a plan view of crimping pliers in accordance with this invention, shown with surgical cable installed in the crimping pliers, with a cable loop shown in the process of being tightened about a bone at a surgical site by the crimping pliers;

FIG. 2 is a fragmentary elevational view of the front jaws of the surgical pliers of FIG. 1, rotated 90 degrees about the longitudinal axis of the surgical pliers;

FIG. 3 is an exploded, fragmentary perspective view of the capstan means found on the end of one operating handle of the surgical pliers of FIG. 1, plus a torque wrench which may be applied to turn the winding shaft through a torque extension member in accordance with this invention;

FIG. 4 is a perspective view of an alternate design of capstan moans carried on the handle of crimping pliers similar to those of FIG. 1;

FIG. 5 is a fragmentary elevational view taken along line 5—5 of FIG. 4; and

FIG. 6 is a fragmentary perspective view of the front end of crimping pliers jaws similar to FIG. 1, with the cable loop being formed about a bone in a modified manner.

DESCRIPTION OF SPECIFIC EMBODIMENTS

Referring to FIGS. 1 and 2, ratchet-type crimping pliers 10 are shown, comprising a pair of operating handles 12, 14 and connected, opposed crimping jaws 16, 18. The mechanism of crimping pliers 10 may be substantially that of the prior art, where the rotating of handles 12, 14 about pivot 20 causes additional pivoting of jaws 16, 18 about the respective pivots 22, 24. Center pivot strap 26 is provided for opening and closing of jaws, 16, 18 with high mechanical advantage, for crimping of a tubular crimp member 28 about cable 30, which passes through tubular crimp member 28. Crimp member 28 occupies opposed recesses 32, 34 in the front end of jaws 16, 18. Except as otherwise described herein, crimping pliers 10 may be of entirely conventional construction.

Cable 30 is preferably made of multistrand stainless steel wire, for example 7×7 cable (7 strands of 7 wires each). The cable may be swedged to reduce its surface roughness and may typically have a diameter of about 0.04 inch. Such cable may have a high flexibility, which is desired for holding bones tighter together for faster healing, and also for avoiding damage to surrounding tissues, for example a spinal cord, as the cable is applied into a loop about the surgical site.

If desired, a stiffened leader may be placed on the end of the cable which is opposed to the cable loop 32 to facilitate surgical installation of the cable, and then its passage through tubular crimp member 28. In the embodiment of FIG. 1, the end of cable 30 which participates in loop 36 defines a small permanent loop 38 which is held with a crimp or the like, as shown, so that cable 30 may pass through loop 38 prior to passing through crimp member 28.

Thus, bone 40 at the surgical site may be looped with cable 30 by the surgeon, after which the cable end 42 which is opposed to loop 36 may be passed through tubular crimp member 28 while mounted in recesses 32, 34 of the jaws 16, 18. The remaining cable 30 passes rearwardly to engage capstan 44 which is mounted at the rear of handle 14 of the crimping pliers. Capstan 44 defines a winding shaft 46 which may have an aperture 48 or the like to receive cable 30. Winding shaft 46 projects through an aperture into housing 50 where it carries a gear 52. Gear 52, in turn, engages with a central worm section 54 of a rotatable handle 56 which includes two knurled ends 58 which project outwardly from opposite sides of housing 50. A self-locking worm gear arrangement is preferred, for achieving a desired, nonslipping tension setting on the cable. Thus, capstan 44 may be operated to cause winding shaft 46 to tighten cable 30. As the cable 30 resultingly slides through tubular crimp member 34 held in jaws 16, 18 of the crimping pliers, loop 36 is tightened around bone 40 to any desired degree in a manner corresponding to the tension placed on cable 30 by capstan 44.

It can be seen particularly from FIG. 2 that tubular crimp member 28 defines a transverse, typically circular, flange 60 on its front end. Also, it can be seen that crimp member 28 is held by opposed recesses 32, 34 at an angle of about 20 degrees to the longitudinal axis 61 of jaws 16, 18 and crimping pliers 10. Thus, cable 30 can be seen to exit rearwardly from jaws 16, 18 at an oblique angle, which facilitates its rearward extension along the side of crimping pliers 10 to capstan 44. It can also be seen in FIG. 1 how the front flange 56 of tubular crimp member 28 can impinge directly against the permanent loop 38, which participates in the formation of the larger loop 36 of the cable. Because of this direct contact between the front flange 56 of crimp member 28 against cable looped end 38, no inherent slack is created in the process of tightening loop 36, and then crimping crimp member 28 to permanently hold loop 36 at the desired level of tightness.

Referring again to FIG. 3, it can be seen that rotatable handle 56 may define at each projecting end 58 a hexagonal hole 62, or any other structure of desired shape, to engage a torque wrench 64, or the connecting shaft 66 of a torque handle 68, to rotate handle 56 as desired to wind cable 30 to a predetermined tension which can be that which is indicated on the torque wrench 64. Torque handle 68 itself may define a slip arrangement, including a tapered, threaded end 70 defining a plurality of longitudinal slots 72, so that the tapered end 70 defines separate, threaded fingers 73 between slot 72, which fingers are inwardly flexible. Nut 74 is threaded on the threads of fingers 73, with the threads of finger 73 and the corresponding threads of nut 74 being tapered of frustoconical shape. Hexagonal shaft 66 has a cylindrical portion which rotates within fingers 73, which are pressed by nut 74 against that portion of shaft 66 to provide the desired, predetermined rotational slippage at excess torque so that a predetermined maximum torque is imposed on capstan 44 by torque handle 68. The novel torque handle 68 can serve as a torque wrench in its own right, being adjustably set by nut 74 so that a conventional torque wrench 64 can be used to merely calibrate handle 68 to a predetermined torque value. Also, as a further advantage, torque handle 66 can be made of an all-metal, autoclavable construction.

Torque wrench 64 comprises a head and hex shaft 65 for fitting into the upper end of torque handle 68 for rotation thereof. Then, one may twist handle 67, causing bar 69 to bend relative to a stylet 71. An indicator plate 73 is provided to measure the amount of bending bar 69 relative to stylet 71, with a indicator readout of torque being thus provided. Torque wrench 64 shares with torque handle 68 the advantage that it can be autoclaved without damage.

Lower extension 75 of shaft 66 may provide a smaller hex end, to permit torque handle 68 to be used to install and remove bone screws during the same surgical procedure. The hex aperture 62 within each of handles 58 may provide a corresponding recess to receive shaft extension 67.

Accordingly, by this invention, one may loop cable 30 around the bone 40 to form the desired loop, with cable end 42 being threaded through crimp member 28 and passed along crimping pliers 10 down to capstan 44. By this means, a loop 36 may be loosely placed around bone 40 at the surgical site for binding of bones together or the like. Then, capstan 44 may be operated, preferably with torque handle 68, causing cable 30 to be drawn rearwardly through crimp member 28 until loop 36 has tightened around bone 40 to a degree of tension as predetermined by torque wrench 64. One then squeezes handles 12, 14 of the crimping pliers to collapse tubular crimp member 34 in a preferably hexagonal cross section pattern so that crimp member 34 is firmly seated on cable 30. In fact, the bond between such a crimped crimp member 34 can be stronger than the tensile strength of cable 30 itself. Following this, one cuts cable 30 at the position as indicated by arrow 76, generally flush with the inner end of tubular crimp member, and the loop of surgical cable is permanently positioned in its desired place.

Turning to FIGS. 4 and 5, an alternate capstan structure is disclosed. Operating handle 14 of crimping pliers 10 carries a simplified capstan 78 which comprises a winding shaft 80, and a rotatable handle 82 connected together by a gear system. Specifically, rotatable handle 82 defines a worm gear shaft 84 which rotates a gear 86 carried on rotary shaft 88 which terminates within spaced fingers 92 in rotatable relation thereto. Nut 90 has a tapered, frustoconical, internal thread. Winding shaft 80 defines a frustoconical, external thread carried on the spaced fingers 92 to function in a manner similar to the structure and function with respect to fingers 73 and nut 74, to frictionally hold shaft 88 to an adjustable, predetermined torque. Thus, capstan 78 also defines a slip mechanism to avoid excess torque as cable 30 is wound to tightness, to collapse loop 36 by the simplified manual system of FIGS. 4 and 5.

Turning to FIG. 6, a new embodiment of mechanism for forming a loop 36a in cable 30a is shown, for use with crimping pliers 10. The ends of jaws 16, 18 of pliers 10 are shown, as well as the front flange 60 of a mounted crimp member 28, of identical design to the previous crimp member, and canted at the 20 degree angle as illustrated in FIG. 2.

In this embodiment, one end of cable 36a carries a stop member 94. Bar member 96 defines a pair of transversely mounted apertures through which cable 36a passes. A portion of cable 36a next to stop member 94 passes through the first transverse aperture, as shown, with stop member 94 preventing the one end of cable 30a from passing through the aperture. The cable then loops around in its loop 36a, to pass through the second transverse aperture of bar 96, as shown. Immediately thereafter, it passes through the crimp member carried in jaws 16, 18, the front end 60 of which is shown in FIG. 6. From there, cable 30a extends rearwardly to a capstan of a type shown in the other drawings.

As the cable loop of FIG. 6 is tightened by a capstan mounted on pliers 10, bar 96 assumes a configuration as shown which is generally parallel to the bone 40 which is being looped. Thus, as the loop is tightened the respective portions of cable 36a (as they project out of the apertures of bar 96) project in directions which are not radially outwardly from bone 40, but rather in a direction similar to tangent lines to the bone. Accordingly, the projecting cable ends of the finished, emplaced surgical cable loop are less likely to damage tissue in the body by abrasion or the like. Since they do not project outwardly in a radial manner.

Handle 12 of crimping pliers 12 is shorter than handle 14 to provide room for torque handle 68 as it engages the right hand handle 58.

Accordingly, it becomes possible in a surgical procedure to set a specific tension on torque handle 58 by adjusting nut 74, and then testing the resulting, maximum torque with torque wrench 64 adjusting nut 74 until a desired maximum torque of torque handle 68 is achieved. Then, torque handle 68 may be used to engage either of handles 58 to tighten cable 30 by applying torque up to the predetermined maximum. If, during the surgical procedure, it is decided that the torque is wrong and that the tension on loop 36 should be either increased or released, one may adjust nut 74 to provide a different maximum torque, measuring it as desired with torque wrench 64, to provide a different but predetermined tension to cable 30.

Self-locking worm gear 54 maintains whatever tension is desired on cable 30 except when positively adjusted by handles 58.

If desired, capstan 44 may be replaced by a ratchet system, as an alternative embodiment.

A ratchet-type crimping pliers 10 is generally preferred over other mechanisms since crimp member 28 may be held under low pressure in such crimping pliers until released by operation of ratchet release 97. Cable 30 may be fed through the loop eyelet 38 or apertured member 96 to form a snug connection around the object 40 to be tightened by handling of the cable. Then, one may operate capstan 44 to obtain the desired amount of tension, following which crimper 10 is fully closed to permanently seal crimp 28 against the cable. Then the ratchet release 97 is actuated, and the crimper is spring-opened.

The nurse can preload the crimp into the crimper under low tension and then provide it to the surgeon at the appropriate time in the operation.

Thus, an improved method and apparatus for the emplacement of surgical wire is provided, having the advantages as previously discussed.

As another advantage of the system of this invention, the looped cable is relatively easily removed from the bone, if that is needed.

The above has been offered for illustrative purposes only, and is not intended to limit the scope of the invention of this application, which is as defined in the claims below.

That which is claimed is:

1. Crimping pliers which comprises a pair of operating handles and connected, opposed jaws, said jaws defining opposed recesses for carrying and crimping a tubular crimp member by manual pressure on the operating handles, and capstan means carried on one of said handles for winding a cable which passes through a tubular crimp member carried in said jaws, said capstan means comprising a winding shaft for retaining and winding said cable, a rotatable handle, and self-locking worm gear means for rotating said winding shaft in either direction with rotation of said handle.

2. The crimping pliers of claim 1 in which said opposed recesses are positioned to carry said crimp member at an acute angle to the axis of said crimping pliers jaws.

3. The crimping pliers of claim 2 in which said acute angle is 10 to 50 degrees.

4. The crimping pliers of claim 2 which hold said recesses a tubular crimp member in combination therewith, said member defining a transverse flange on its front end, and a cable defining a loop forward of said crimp member, said cable passing through said crimp member and being wound on said capstan means.

5. The crimping pliers of claim 1 in which said rotatable handle defines a connection for receiving wrench means to rotate said handle.

6. The crimping pliers of claim 5 in which said rotatable handle extends outwardly from two opposed sides of the operating handle that carries said capstan means, for rotation of the rotatable handle from either side.

7. The crimping pliers of claim 1 in which said opposed recesses are shaped to press said tubular crimp member into hexagonal cross sectional configuration upon crimping.

8. Crimping pliers which comprises a pair of operating handles and connected, opposed jaws, said jaws defining opposed recesses for carrying and crimping a tubular crimp member by manual pressure on the operating handles, said opposed recesses being positioned to carry said crimp member at an acute angle to the axis of said crimping pliers jaws, and capstan means carried on one of said handles for winding a cable which passes through a tubular crimp member carried in said jaws, said capstan means comprising a winding shaft for retaining and winding said cable, a rotatable handle, and means for rotating said winding shaft with said rotation of said handle.

9. The crimping pliers of claim 8 in which said acute angle is 10 to 50 degrees.

10. The crimping pliers of claim 9 which holds in said recesses a tubular crimp member in combination therewith, said member defining a transverse flange on its front end, and a cable defining a loop forward of said crimp member, said cable passing through said crimp member, and being wound on said capstan means.

11. The crimping pliers of claim 10 in which said cable loop is defined with a bar member defining a pair of spaced, transverse apertures, said cable extending through both apertures.

12. The crimping pliers of claim 11 in which said rotatable handle defines a connection for receiving wrench means to rotate said handle, and in which said rotatable handle extends outwardly from two opposed sides of the operating handle that carries said capstan means, for rotation of the handle from either side.

13. The crimping pliers of claim 9 in which said rotatable handle defines a connection for receiving wrench means to rotate said handle, and in which said rotatable handle extends outwardly from two opposed sides of the operating handle that carries said capstan means, for rotation of the rotatable handle from either side.

14. The crimping pliers of claim 8 in which said opposed recesses are shaped to press said tubular crimp member into hexagonal cross sectional configuration upon crimping.

15. The crimping pliers of claim 8 in which said means for rotating said winding shaft comprise a self-locking worm gear whereby said winding shaft is capable of rotating in either direction without slippage apart from deliberate rotation.

16. A crimping pliers which comprises a pair of operating handles and connected, opposed jaws, said jaws defining opposed recesses for carrying and crimping a tubular crimp member by manual pressure on the operating handles, said opposed recesses being positioned to carry said crimp member at an acute angle to the axis of the jaws of said crimping pliers.

17. The crimping pliers of claim 16, further including capstan means carried on one of said handles for winding a cable which passes through a tubular crimp member carried in said jaws.

18. The crimping pliers of claim 16 in which said opposed recesses are shaped to press said tubular crimp member into hexagonal cross sectional configuration upon crimping.

19. The crimping pliers of claim 18 in which said capstan means comprises a rotatable handle defining a worm gear shaft which rotates a gear carried on a rotary shaft, said rotary shaft terminating within spaced fingers in rotatable relation thereto, whereby said fingers frictionally hold said shaft to an adjustable, predetermined torque.

20. The crimping pliers of claim 2 in which means are provided to cause said winding shaft to slip rather than rotating with said rotatable handle upon the encountering of a predetermined maximum torque.

* * * * *